United States Patent [19]

Scher et al.

[11] Patent Number: 4,933,167

[45] Date of Patent: Jun. 12, 1990

[54] PESTICIDE COMPOSITIONS

[76] Inventors: Herbert B. Scher, 1028 Wickham Dr., Moraga, Calif. 94556; Marius Rodson, 611 Liberty St., El Cerrito, Calif. 94530; Ronald L. Morgan, 115 S. Mayfair #5, Daly City, Calif. 94015

[21] Appl. No.: 271,353

[22] Filed: Nov. 14, 1988

Related U.S. Application Data

[63] Continuation of Ser. No. 121,369, Nov. 16, 1987, abandoned, which is a continuation of Ser. No. 808,966, Dec. 16, 1985, abandoned, which is a continuation of Ser. No. 625,411, Jul. 2, 1984, abandoned, which is a continuation-in-part of Ser. No. 516,487, Jul. 11, 1983, abandoned.

[51] Int. Cl.$^5$ .............................................. A01N 57/18
[52] U.S. Cl. ..................................... 424/10; 514/140; 514/141; 424/78
[58] Field of Search ............................ 424/10, 45, 78; 514/140, 141; 71/DIG. 1, 64.07, 64.11, 64.13

[56] References Cited

U.S. PATENT DOCUMENTS 3,959,464  5/1976  De Savigny .
4,140,516  2/1979  Scher .
4,285,720  8/1981  Scher .

*Primary Examiner*—Allen J. Robinson
*Attorney, Agent, or Firm*—Denis A. Polyn

[57] ABSTRACT

Toxicant, especially pesticide compositions, having lowered dermal toxicity are provided. The compositions include a microencapsulated lipophilicpesticide, a hydrophilic surfactant and water. Methods for reducing the dermal toxicity of microencapsulated lipophilic toxicants, especially pesticides are provided. Methods for controlling insect pests using the disclosed compositions are provided.

3 Claims, No Drawings

PESTICIDE COMPOSITIONS

CROSS-REFERENCE TO RELATED APPLICATIONS

This application is a continuation of application Ser. No. 121,369, filed Nov. 16, 1987, now abandoned; which is a continuation of application Ser. No. 808,966, filed Dec. 16, 1985, now abandoned.

This application is a continuation-in-part application of U.S. Ser. No. 516,487, filed July 22, 1983, which is a continuation of application Ser. No. 625,411, filed July 2, 1984, now abandoned; which in turn is a continuation-in-part of application Ser. No. 516,487, filed July 22, 1983, now abandoned.

FIELD OF THE INVENTION

The invention relates to compositions of microencapsulated dermally toxic pesticides that have been additionally safened for handling by addition thereto of a hydrophilic surfactant and water. More particularly, the invention relates to compositions comprising microencapsulated dermally toxic pesticides that have been safened for handling by addition thereto of a hydrophilic surfactant and water.

BACKGROUND OF THE INVENTION

A wide variety of pesticides are commonly used in agronomic and horticultural pursuits. As used herein the term "pesticide" means any chemical compound or composition which displays biological activity in an agricultural field site or at any locus where control of biological growth is desired. The biological activity or control contemplated herein includes all forms of growth modification, ranging from regulation and retardation to killing, and extends to all forms of plant and animal life found in an agricultural environment during some time during the pest's life cycle. Pesticides within this invention include anti-foulants, plant growth regulants, soil fumigants, molluscicides, insecticides, herbicides, fungicides, rodenticides, nematocides, algicides, predator control agents, and insect and animal repellents. Additional biologically active compounds can also be present in admixture with the primary ingredient, such as synergists, antidotes, fertilizers, soil life extenders, and additional pesticides.

The term "biologically effective amount" is used herein to denote any quantity of pesticide, pesticide composition, concentrate, or emulsion, which when applied to an agricultural site in any conventional manner causes the occurrence of one or more of the biological effects mentioned above. As further explained in the latter portion of this specification, the quantity of pesticide applied in a given situation will depend on the pesticide itself, on the type of biological activity inherent in the pesticide, and the degree of such activity sought to be achieved. The selection of the proper quantity to be applied, however, is within the expertise of one skilled in the art.

In general if handled carelessly, improperly or in disregard of directions, the pesticide, depending upon its toxicity, may present a hazard to those handling the pesticide whether in packaging it for sale, handling it for shipment, mixing it for field application or applying it in the field. The toxicity of the pesticide will vary depending upon a number of factors, including the inherent toxicity of the pesticide substance at its site of biological action. Various physical properties of the pesticide including the hydrophilic-lipophilic balance of the pesticide affect the adsorption to and absorption by various tissues of the person handling the pesticide compound, and thus affect the toxicity of the compound to the person handling it.

Some pesticides, such as the chlorinated hydrocarbon carbamate insecticides and the organophosphate pesticide compounds, including pyrethroids, phosphonate, organophosphate and organothiophosphate compounds present a problem of dermal toxicity to persons handling these substances. Thus, it is desirable to develop formulations for these pesticide compounds that reduce the dermal toxicity of the compound to persons handling them yet still preserve the pesticidal effectiveness of the compound as applied to the pest or the locus where the pest may be found.

SUMMARY OF THE INVENTION

The inventors have discovered a novel pesticidal composition that maintains high biological effectiveness against pests when used in the field and has reduced dermal toxicity.

The compositions comprise a pesticidally effective amount of a microencapsulated dermally toxic pesticide, a hydrophilic surfactant and water. More particularly, the compositions comprise a bioloqically effective amount of a microencapsulated dermally toxic pesticide, a surfactant having a hydrophilic-lipophilic balance (HLB) of between 17 and 20, and water.

Dermal toxicity includes systemic toxic effects that occur in an animal as a result of dermal contact with a toxic substance for a defined period of time. Dermal toxicity may be defined as the LD-50 (lethal dose to 50% of the animals in a test group) caused by a 24 hour exposure to a toxic substance. Acute dermal toxicity may be defined as 400 mg/kg or less in rabbits.

Pesticides of the general composition include dermally toxic organophosphorous, pyrethroids, phosphonate and thiophosphonate compounds. The following are examples of such compounds, followed in parenthesis by their common names, where available:

S-tert-butylthiomethyl O,O-diethyl phosphorodithioate (terbufos)

O,O-diethyl-O-4methylsulphinylphenyl phosphorothioate (fensulfothion)

O,O-diethyl O-2-isopropyl-6-methylpyridimidin-4-yl phosphorothiaote (diazinon)

O,O-diethyl S-2-ethylthioethyl phosphorodithioate (disulfoton)

S-chloromethyl O,O-diethyl phosphorodithiaote (chlormephos)

O-ethyl S,S-dipropyl phosphorodithiaote (ethoprophos)

O,O-diethyl S-ethylthiomethyl phosphorodithiaote (phorate)

O-(4-bromo 2-chlorophenyl) O-ethyl S-propyl phosphorodithiaote (prophenofos)

S-1,2-di(ethoxycarbonyl)ethyl O,O-dimethyl phosphorodithioate (malathion)

O,O,O',O'-tetraethyl S,S"-methylene di(phosphorodithioate) (ethion)

O-(4-bromo-2,5-dichlorophenyl) O,O-dimethyl phosphorothioate (bromophos-ethyl)

S-4-chlorophenylthiomethyl O,O-diethyl phosphorodithioate (carbophenothion)

2-chloro-1-0(2,4-dichlorophenyl)vinyl diethyl phosphate (chlorphenvinphos)

O-2,5-dichloro-4-(methylthio) phenyl O,O-diethyl phosphorodithioate (chlorthiophos)
O-4-cyanophenyl O,O-dimethyl phosphorothiaote (cyanophos)
O,O-dimethyl O-2-methylthioethyl phosphorothioate (demiphion)
O,O-diethyl O-2-ethylthioethyl phosphorothioate (demeton)
O-2,4-dichlorophenyl O,O-diethyl phosphorothioate (dichlorofenthion)
O-2,4-dichlorophenyl 0-ethyl phenylphosphonothioate (EPBP)
O,O-diethyl 0-5-phenylisoxazol-3-yl phosphorothioate (isoxathion)
1,3-di(methoxycarbonyl)-1-propen-2-yl dimethyl phosphate
1,4-dioxan-2,3-diyl S,S-di(o,O-diethyl phosphorothioate (dioxathion)
O,O-dimethyl-0-4-nitro-m-tolyl phosphorothioate (fenitrothion)
O,O-dimethyl 0-4-methylthio-m-tolyl phosphorothioate (fenthion)
O-(5-chloro-1-isopropyl-1,2,4-triazol-3-yl) O,O-diethyl phosphorothiaote (isazophos)
S-2-isopropylthioethyl O,O-dimethyl phosphorodithiaote (isothioate)
4-(methylthio)phenyl dipropyl phosphat (propaphos)
1,2-dibromo-2,2-dichloroethyl dimethyl phosphate (naled)
O,O-diethyl -cyanobenzylideneamino-oxyphosphonothioate (phoxim)
O,O-diethyl O-4-nitrophenyl phosphorothiaote (parathion)
O-2-diethylamino-6-methylpyrimidin-4-yl O,O-diethyl phosphorothiaote (pirimiphos-ethyl)
O-2-diethylamino-6-methylpyrimidin-4-yl O,O-dimethyl phosphorothiaote (pirimiphos-methyl)
O,O,O',O'-tetraethyldithiopyrophosphate (sulfotep)
O,O,O',O'-tetramethyl 0,0'-thiodi-p-phenylene diphosphorothiaote (temephos)
S-2-ethylthioethyl O,O-dimethyl phosphorodithioate (thiometon)
O,O-diethyl O-1-phenyl-1,2,4-triazol-3-yl phosphorothioate (triazophos)
O-ethyl O-2,4,5-trichlorophenyl ethylphosphonothiaote (trichloronate)
(±)-3-allyl-2-methyl-4-oxocyclopent-2-enyl (±)-cis,-trans-chrysanthemate (allethrin)
(±)-3-allyl-2-methyl-4-oxocyclopent-2-enyl (±)-trans-chrysanthemate (bioallethrin)
3-phenoxybenzyl (±)-cis,trans-chrysanthemate (phenothrin) pyrethrins
2-(2-butoxyethoxy)ethyl thiocyanate
isobornyl thiocyanoacetate (terpinyl thiocyanoacetate)
carbon disulfide
2-(4-tert butylphenoxy)cyclohexyl prop-2-ynyl sulphite (propargite)
4,6diinitro-6-octylphenyl crotonates (dinocap)
ethyl 4,4'-dichlorobenzilate (chlorobenzilate)
S,S,S-tributyl phosphorotrithioate
tributyl phosphorotrithioite (merphos)
copper naphthenates
5-ethoxy-3-trichloromethyl-1,2,4-thiadiazole (etridiazole)
O-ethyl S,S-diphenyl phosphorodithioate (edifenphos)
6-butoxycarbonyl-2,3-dihydro-2,2-dimethylpyran-4-one (butopyronoxyl)
N,N-diethyl-m-toluamide (deet)
dibutyl phthalate
dibutyl succinate
1,5a,6,9,9a,9b-hexahydro-4a(4H)-dibenzofurancarboxaldehyde
dipropyl pyridine-2,5-dicarboxylate Other dermally toxic pesticide compounds are exemplified by the following herbicide compounds:
2-propene-1-ol, orvinylcarbinol (allylalcohol)
2-sec-butyl-4,6-dinitrophenol (dinoseb)
2-tert butyl-4,6-dinitrophenol (dinoterb)
4,6-dinitro-o-cresol (DNOC)
2-chloro-N-isopropylacetanilide (propachlor)
S,S,S-tributyl phosphorothioate
2-chloro-N,N-diallyl acetamide (Randox)
2-chloro-2',6'-diethyl-N-(butoxymethl) acetanilide (butachlor)

Of the many different types of pesticides useful in the present composition, certain classes are preferred. One preferred class is that of organcephosphorus compounds, particularly those of the formula:

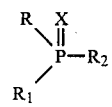

in which X is oxygen or sulfur; and R, $R_1$ and $R_2$ are independently selected from the group consisting of $C_1$–$C_6$ alkyl, $C_1$–$C_6$ alkoxy, $C_1$–$C_6$ alkylthio, $C_2$–$C_6$ alkenyl, $C_2$–$C_6$ alkenoxy, $C_2$–$C_6$ alkenylthio, phenyl, phenoxy, phenylthio, $C_7$–$C_9$ phenylalkyl, $C_7$–$C_9$ phenylalkoxy, alkylthio, each member of such group optionally substituted with up to three substituents selected from halogen, $C_1$–$C_4$ alkyl, $C_1$–$C_4$ alkoxy, cyano, and nitro. The terms "alkyl," "alkoxy," etc., are intended to include both straight-chain and branched-chain groups, and all carbon atoms ranges are inclusive. More preferred organophosphorus compounds are those in which X is sulfur, and R, $R_1$ and $R_2$ are independently $C_1$–$C_4$ alkoxy or phenoxy, the phenyl ring optionally substituted with up to three groups selected from $C_1$–$C_3$ alkyl, nitro, cyano, and halogen. Highly preferred are those in which X is sulfur, R is $C_1$–$C_4$ alkoxy, $R_1$ is $C_1$–$C_4$ alkoxy, and $R_2$ is phenoxy substituted with up to three substituents selected from $C_1$–$C_3$ alkyl and nitro. The most highly preferred are compounds of the general formula:

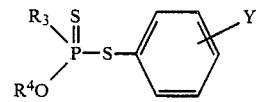

wherein $R_3$ and $R_4$ are selected from the group consisting of methyl and ethyl and Y is selected from the group consisting of hydrogen and alkyl groups having up to 4 carbon atoms.

As was indicated above, surfactants of the general composition have an HLB of between 17 and 20. Such surfactants are, for example, alkyl and dialkylphenoxy poly(ethyleneoxy) ethanols. Suitable surfactants of the above-mentioned HLB range are exemplified by surfactants of the following structural formula

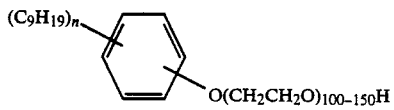

wherein n is 1 or 2.

Further examples of appropriate surfactants according to the invention are summarized in Table I.

TABLE I

| HLB | Commercial Name | Structure |
|---|---|---|
| 17.9 | Myrj 53 | polyoxyethylene (50) stearate |
| 18.0 | Etocas 100 | ethoxylated (100) castor oil |
| 18.0 | Lantrol AWS | alkoxylated lanolin oil |
| 18.0 | Veronic L167 | ethoxylated coco mono-glyceride |
| 18.1 | Alcasurf CO200 | ethoxylated castor oil |
| 18.1 | Chemmax CO-200/50 | ethoxylated castor oil |
| 18.1 | Pegosperse CO200 | POE 200, castor oil |
| 18.1 | Veronic Li48 | ethoxylated mono and diglyceride |
| 18.0 | Tergitol 15-S-50 | secondary alcohol PEG ether |
| 18.3 | Kessco polyethylene glycol | esters, PEG 4000 monoleate |
| 18.8 | Brig 700 | polyethylene 100 stearyl ether |
| 18.8 | Kessco PEG esters | PEG monostearate |
| 18.5 | Pluronic L-35 | |
| 17.0 | Pluronic P-65 | |

In addition to the dermally toxic microencapsulated pesticide and the surfactant having an HLB between 17 and 20, the compositions according to the invention further comprise water.

A representative method for the production of a microencapsulated dermally toxic pesticide of the compositions according to the invention is described in detail in U.S. Pat. No. 4,285,720 which is herein incorporated by reference.

The pesticides of the compositions according to the invention are microencapsulated in microcapsules comprised of a polymer. As used herein the term "microcapsule" is intended to mean the polymer wall and the pesticide contained therein. Polymers useful in the composition according to the invention include a wide variety of types, including cellulosic materials, polyolefins, polyacrylonitriles, polyacrylates, polyethers, polyethers, polyamides polyureas, polysiloxanes, polyurethanes and combinations thereof. Examples include ethyl cellulose, nitrocellulose, cellulose acetate butyrate, polystyrene, polybutadiene, polyisoprene, polyethylene, polypropylene, polyvinyl acetate, polyvinyl alcohol, polyvinyl chloride, polyethyl methacrylate, polymethyl methacrylate and combinations thereof, copolymers of vinyl acetate and vinyl chloride, butadiene-styrene copolymers, butadiene-acrylonitrile copolymers, copolymers of polyisocyanates and diisocyanates such as polymethylene polyphenyl isocyanate-tolyl diisobyanate copolymers, vinylidene chloride-vinyl chloride copolymers and condensates of urea-formaldehyde prepolymer which may be further self-condensed or condensed with di- and polyhdyroxy- and/or di- and polysulfhydral-containing molecules such as ethylene glycol and castor oil and/or pentherythritol tetrakis (mercaptopropionate) (Mercaptate® Q43-ester Cincinnati, Ohio, Milacron). Preferred polymers are copolymers of polyisocyanate and diisocyanate.

The extent of cross-linking of the polyurea polymer and the amount of the pesticide in the microcapsules may vary. Furthermore, the polyurea wall may be within the range of from about 2.0% to about 50% of the microcapsule on a weight basis. It is, however, preferable that the range of polyurea wall be within a range from about 2.5% to about 10% of the microcapsule on a weight basis. Most preferred is a polyurea wall in a range of between 5% and 6.5% of the microcapsule on a weight basis.

The pesticide compositions according to the invention may have various amounts of microencapsulated pesticide, hydrophilic surfactant and water. Expressed as a weight percent of the whole composition, the surfactant may range between about 0.1% and about 10% with a preferred range of between 1% and 6% and an optical range of between 2% and 5%, depending upon the exact composition of the surfactant.

The amount of pesticide compound in the pesticidal composition may vary depending on the specific activity of the pesticide under field conditions and the duration desired for the pesticidal activity. In general, the pesticide may comprise between 10% and 98% of the microcapsule on a weight basis and from 0.1% to about 75% of the composition on a weight basis.

The amount of water in pesticidal compositions may vary between 20% and in excess of 99%, as the composition may be substantially diluted when used in a sprayable form.

The invention will be better understood with respect to the following example which is intended by the inventors to be exemplary only and non-limiting.

EXAMPLE I

A pesticidal composition, designated Composition A, containing a microencapsulated dermally toxic pesticide, in which the pesticide comprised about 54% on a weight basis of the composition and the microcapsule wall comprised about 3.7% on a weight basis of the composition (6.5% of the microcapsule) was prepared. The pesticide was Dyfonate® (o-ethyl-S-phenylethyl phosphonodithioate, a product of Stauffer Chemical Company, the synthesis of which is disclosed in U.S. Pat. No. 2,988,474 which is incorporated herein by reference), at about 93.0 wt. % minimum purity, and the microcapsule wall was a polyurea polymer formed by the reaction of polymethylene polyphenylisocyanate (P) and tolyl diisocyanate with water (P/T ratio of 1.5). The microencapsulation of the pesticide was carried out in accordance with the disclosure of U.S. Pat. No. 4,285,720, using as the emulsifier Tergitol 15-S-7®, a secondary alcohol PEG ether. The emulsifier concentration was about 0.3% by weight based on the aqueous phase. The microencapsulation was carried out in a mixture having the following components on weight percent basis:

| Weight % | Microencapsule Mixture |
|---|---|
| 56.03 | technical Dyfonate (93.0 wt. % minimum purity) |
| 2.34 | polymethylene polyphenyl isocyanate |
| 1.55 | tolyl diisocyanate |
| 0.81 | protective colloids (polymethylvinyl ether-maleic acid and polyvinyl alcohol) |
| 0.12 | emulsifier (polyethylene glycol of secondary alcohol) (Terigitol 15-S-7) HLB = 12.1 |
| 39.44 | water |
| 100.00 | |

After the microcapsules were made in accordance with U.S. Pat. No. 4,285,720 a hydrophilic surfactant having the structural formula

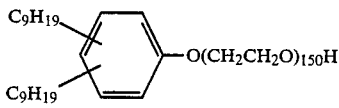

was added to a concentration of 3.0 wt. % of the entire mixture. On a weight basis the components of Composition A had the following proportions:

| Weight % | |
|---|---|
| 53.65 | O-ethyl-S-phenyl phosphonodithioate |
| 3.23 | polyurea wall |
| 0.78 | protective colloids (polymethylvinyl ether-maleic acid and polyvinyl alcohol) |
| 0.05 | xantham gum |
| 0.33 | attapulgite clay |
| 0.97 | buffering agents (sodium carbonate and sodium hydroxide) |
| 0.02 | sodium tripolyphosphate |
| 0.01 | aluminum sulfate |
| 0.12 | emulsifier (HLB = 12.1) polyethylene glycol ether of secondary alcohol |
| 2.78 | surfactant HLB = 19 |
| 37.47 | water |
| 100.00 | |

A second pesticidal composition, designated Composition B, was made up having the same composition as Composition A except that the surfactant (alkyl phenoxy poly(ethyleneoxy)ethanol) had the structural formula

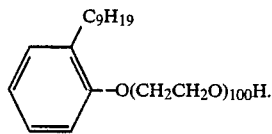

A third pesticidal composition, designated Composition C, was made up having the same composition as Composition B except that the surfactant comprised about 2% (wt/ %).

Two control compositions were also made up. Control 1 was comprised of the same composition as Composition A but lacked the hydrophilic surfactants indicated in Compositions A, B and C. Control 2 also comprised the same composition as Control 1 except that the microcapsule wall comprised about 5% of the microcapsule on a weight basis.

· Dermal Toxicity

Acute dermal toxicity was determined in accordance with the Environmental Protection Agency's Proposed Guidelines for Registering Pesticides in the U.S.; Hazard Evaluation Humans and Domestic Animals, *Fed. Reg.* 43:163, 37336–37402 (Aug. 22, 1978).

Albino rabbits (Stauffland White strain, Phillips Rabbitry, Soquel, Calif.) were housed in temperature controlled animal rooms (65°–70° F.), two to a cage in suspended steel cages (24" ×16.5" ×14"). Feed (Special Mixture, Gunter Bros., Morgan Hill, Calif.) and water were provided ad libitum.

Prior to treatment, the rabbits were randomly selected and individually identified using numbered ear tags. The day before treatment the skin areas to be treated were closely clipped and the rabbits were fasted overnight with water available.

The first dose tested was 2,000 mg/kg in 10 rabbits, 5 males and 5 females. Doses were selected at logarithmically spaced intervals decreasing from 2,000 mg/kg. These levels selected produced at least three test groups with mortality rates between 10% and 90% and permitted calculation of the $LD_{50}$ (abraded skin and/or intact skin) of males and females with a 95% confidence interval of 20% or less. At least three dose levels and controls were tested.

Four male and four female rabbits were used for each succeeding dose level. In some of the tests, half of the rabbits at each dose level were further prepared by making epidermal abrasions with a needle in a cross-hatch manner over the entire exposure area. The abrasions were sufficiently deep to penetrate the stratum corneum, but not the dermis. A single application of the composition was applied neat to the dose site. The composition was held in contact with the skin by a non-absorbent binder. To insure the integrity of the binder an outer wrapping of gauze was applied. At the end of the 24 hour exposure period, the wrappings were removed and the skin wiped and/or washed to remove any remaining test substance. The animals were then wrapped with fresh gauze which was left in place for 72 hours.

Four rabbits (two of each sex) were sham-treated by wrapping each in a similar manner.

Animals were observed for at least 14 days after dosing or until all signs of reversible toxicity in survivors subsided, whichever occurred later.

Observation for clinical signs and mortality were recorded frequently the first day, and early morning and late afternoon thereafter. The animals were observed once a day during weekends and holidays. All clinical signs were recorded for the onset, duration and severity. Rabbits were weighed on days 0 (prior to treatment), 7, 14 or at death, with the mean body weight calculated for each day.

The acute dermal toxicity in these tests was found to be unaffected by prior abrasion of the skin of the test animals. The results of these tests are reported in Table II.

TABLE II

| Composition | % Wall | P/T | Surfactant | Dermal $LD_{50}$ (mg/kg) and 95% Confidence limits |
|---|---|---|---|---|
| Control 1 | 6.5 | 1.5 | none | 370 (285–480) |
| Control 2 | 5.0 | 1.5 | none | 161 (107–243) |
| Composition A | 6.5 | 1.5 | 3% dialkyl* | 809 (564–1160) |
| Composition B | 6.5 | 1.5 | 3% alkyl** | 500 (—) |
| Composition C | 6.5 | 1.5 | 2% alkyl** | 457 (350–596) |

*dialkylphenoxy poly(ethyleneoxy)ethanol
**alkylphenoxy poly(ethyleneoxy)ethanol Insecticidal Effectiveness The insecticidal effectiveness of the composition was tested in the following manner:

One cubic centimeter (cc) of Western spotted cucumber beetle larvae (*Diabrotica undecimpunctata*) supplied by Mannerheil)]containing about 7,000 eggs was diluted to a final concentration of 250 eggs/cc by suspending 0.5 cc of undiluted eggs in 14 cc of water containing 0.2% Dacagin (Diamond Alkali Co.). Eggs may be stored in this suspension for 5 days at 5° C. without significant loss of viability.

Ten grams (10 g) of moist "Supersoil" (Wonderline, Rod McLellan Co., San Francisco, Calif.) were placed in a one ounce clear plastic cup (Thunderbird Container Corporation, El Paso, Tex.). The test material was dissolved in acetone or an appropriate solvent. A 0.05 milliliter (ml) aliquot of the test sample that had been diluted to the desired concentration was added to the soil. The cup was capped and the soil was mixed on a Vari-Whirl mixer for approximately 15 seconds. An indentation was made on the surface of the soil and 0.2 cc of the egg suspension was added. The eggs were covered with soil and maintained at room temperature (approximately 70° F.). Four days later a section of Romaine lettuce leaf was placed in the treated cups. One week layer the cups were examined for live larvae.

Test concentrations range from 10 ppm down to that at which approximately 50% mortality occurs.

The following compositions were tested: Composition A, Control 2 (both described hereinabove) and Control 3 comprised of the same composition as Control 2 except the microcapsule wall had a P/T ratio of 2.0 and was approximately 10% (wt/%) of the microcapsule. In addition, technical grade Dyfonate ® of at least 93% purity was tested under the same conditions. The results of the test are shown in Table III.

TABLE III

| Composition | Replicate # | 2.44 | 1.95 | 1.56 | 1.25 | 1.00 | LD$_{50}$ |
|---|---|---|---|---|---|---|---|
| Control 3 | 1 | 100 | 100 | 100 | 0 | 0 | 1.56 |
|  | 2 | 100 | 100 | 0 | 0 | 0 |  |
| Control 3 | 1 | 100 | 100 | 0 | 0 | 0 | 1.95 |
|  | 2 | 100 | 100 | 0 | 0 | 0 |  |
| Control 2 | 1 | 100 | 100 | 0 | 0 | 0 | 1.75 |
|  | 2 | 100 | 100 | 0 | 0 | 0 |  |
| Composition A | 1 | 100 | 100 | 0 | 0 | 0 | 1.75 |
|  | 2 | 100 | 100 | 0 | 0 | 0 |  |
| Dyfonate ® (tech) | 1 | 100 | 100 | 100 | 100 | 0 | 1.13 |
|  | 2 | 100 | 100 | 100 | 100 | 0 |  |
| Sham Control | 1 | 0 |  |  |  |  |  |

TABLE III

The results of the test clearly indicate that the effectiveness of the insecticidal composition is not reduced by the surfactant.

It will be readily apparent to those skilled in the art that the insecticidal compositions of the instant invention offer markedly reduced dermal toxicity without significantly reducing the insecticidal effectiveness of the insecticidal compound used in the composition.

What is claimed is:

1. A pesticide composition comprising:
   (a) a microencapsulated O-ethyl-S-phenylethyl phosphonodithioate pesticide compound, said pesticide compound comprising on a weight basis from about 0.1% to about 75% of the composition;
   (b) from about 0.1% to about 10% by weight of said composition of a surfactant compound of the formula

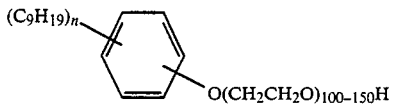

wherein n is 1 or 2; and
   (c) from about 20% to about 99% by weight water.

2. A method of controlling insects comprising applying to the locus where said insects are found during some part o±their life cycle an insecticidally effective amount of an insecticide composition comprising:
   (a) a microeocaspulated O-ethyl-S-phenylethyl phosphonodithioate insecticide compound, said insecticide compound comprising on a weight basis from about 0.1% to about 75% of the composition;
   (b) from about 0.1% to about 10% by weight of said composition of a surfactant compound of the formula

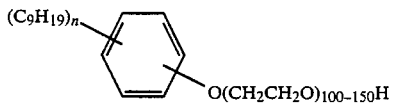

wherein n is 1 or 2; and
   (c) from about 20% to about 99% by weight water.

3. A method of lessening dermal and systemic toxic effects to a mammal coming into contact with a dermally toxic pesticide composition consisting of a microencapsulated dermally toxic O-ethyl-S-phenylethyl phosphonodithioate pesticide compound and water, comprising the steps of admixing with said composition from about 0.1% to about 10% by weight of said composition of a surfactant compound of the formula

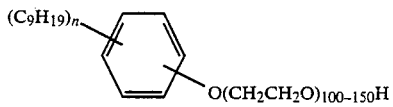

wherein n is 1 or 2.

* * * * *